(12) United States Patent
Steen

(10) Patent No.: US 10,198,853 B2
(45) Date of Patent: Feb. 5, 2019

(54) METHOD AND SYSTEM FOR PERFORMING REAL-TIME VOLUME RENDERING TO PROVIDE ENHANCED VISUALIZATION OF ULTRASOUND IMAGES AT A HEAD MOUNTED DISPLAY

(71) Applicant: General Electric Company, Schenectady, NY (US)

(72) Inventor: Erik Normann Steen, Oestfold (NO)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 169 days.

(21) Appl. No.: 15/452,041

(22) Filed: Mar. 7, 2017

(65) Prior Publication Data

US 2018/0260995 A1 Sep. 13, 2018

(51) Int. Cl.
| | |
|---|---|
| *G06T 15/04* | (2011.01) |
| *G06T 15/06* | (2011.01) |
| *G06T 15/80* | (2011.01) |
| *G06T 15/08* | (2011.01) |
| *G06T 15/20* | (2011.01) |
| *A61B 8/08* | (2006.01) |

(52) U.S. Cl.
CPC .............. *G06T 15/08* (2013.01); *A61B 8/483* (2013.01); *G06T 15/04* (2013.01); *G06T 15/06* (2013.01); *G06T 15/205* (2013.01); *G06T 15/80* (2013.01); *G06T 2210/41* (2013.01); *G06T 2215/16* (2013.01)

(58) Field of Classification Search
CPC .............................. G06T 15/506; G06T 15/50
USPC ....................................................... 345/426
See application file for complete search history.

(56) References Cited

U.S. PATENT DOCUMENTS

| | | | |
|---|---|---|---|
| 9,704,270 B1* | 7/2017 | Main | G06T 9/00 |
| 2011/0228997 A1* | 9/2011 | Sharp | G06T 19/00 |
| | | | 382/131 |
| 2014/0247277 A1 | 9/2014 | Guenter et al. | |
| 2015/0154790 A1* | 6/2015 | Kim | G06T 15/08 |
| | | | 345/424 |
| 2015/0377613 A1* | 12/2015 | Small | A61B 5/1076 |
| | | | 348/45 |

(Continued)

OTHER PUBLICATIONS

Guenter, Brian, et al., "Foveated 3D Graphics," Microsoft Research, 10 pages, Nov. 20, 2012.

*Primary Examiner* — Jin Ge
(74) *Attorney, Agent, or Firm* — McAndrews, Held & Malloy, Ltd.; Jacob Groethe; David Bates

(57) ABSTRACT

A processor receives sensor feedback indicating a focal point of an HMD user. The processor casts rays through an image volume based on the sensor feedback. Each of the rays is associated with a pixel of a rendered image. The rendered image has a first plurality of pixels associated with the rays and a second plurality of unassociated pixels. The rays comprise a first portion cast at or near the focal point and a second portion that is cast farther away from the focal point. A first spacing between rays of the first portion is less than a second spacing between rays of the second portion. The processor determines color values corresponding with each of the first plurality of pixels associated with the rays. The processor determines color values corresponding with each of the second plurality of unassociated pixels of the rendered image. The HMD displays the rendered image.

20 Claims, 9 Drawing Sheets

(56) References Cited

U.S. PATENT DOCUMENTS

2016/0217563 A1\* 7/2016 Wahrenberg ............ G06T 15/08
2017/0132830 A1\* 5/2017 Ha ........................ G06T 15/005
2017/0285735 A1\* 10/2017 Young ..................... G06F 3/013

\* cited by examiner

METHOD AND SYSTEM FOR PERFORMING REAL-TIME VOLUME RENDERING TO PROVIDE ENHANCED VISUALIZATION OF ULTRASOUND IMAGES AT A HEAD MOUNTED DISPLAY

FIELD

Certain embodiments of the disclosure relate to ultrasound imaging. More specifically, certain embodiments of the disclosure relate to a method and system for providing enhanced visualization of ultrasound images at a head mounted display by performing real-time volume rendering. The method and system may be operable to perform volume ray casting with a greater amount of rays cast near a user focal position and reducing the quantity of rays cast as the distance from the user focal position increases. In various embodiments, the sampling distance along the part of the ray that lies within the ultrasound image volume may increase as the distance of the ray from the user focal position increases.

BACKGROUND

Ultrasound imaging is a medical imaging technique for imaging organs and soft tissues in a human body. Ultrasound imaging uses real time, non-invasive high frequency sound waves to produce a two-dimensional (2D) image and/or a three-dimensional (3D) image. The 2D and/or 3D ultrasound images may be presented at a display system to assist with diagnosing causes of pain, swelling, and infection in the internal organs of a body. Ultrasound images may be viewed at a display system to examine a baby in pregnant women and the brain and hips in infants. Ultrasound images may also be used at display systems to help guide biopsies, diagnose heart conditions, and assess damage after a heart attack, among other things.

Ultrasound images are typically presented at a flat panel display screen, such as a liquid crystal display (LCD) or a light emitting diode display (LED). Head mounted virtual reality displays (HMDs) may provide users an intuitive way to visualize complex data, such as ultrasound images. Typical HMDs provide a sustained steady display frame rate of 90-120 Hz to prevent motion sickness. Rendering complex volume data with sufficient spatial resolution at this high framerate for each eye, however, is computationally expensive, increasing the graphics processing unit (GPU) workload by at least one order of magnitude compared to the GPU workload for standard 2D displays.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for performing real-time volume rendering to provide enhanced visualization of ultrasound images at a head mounted display, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
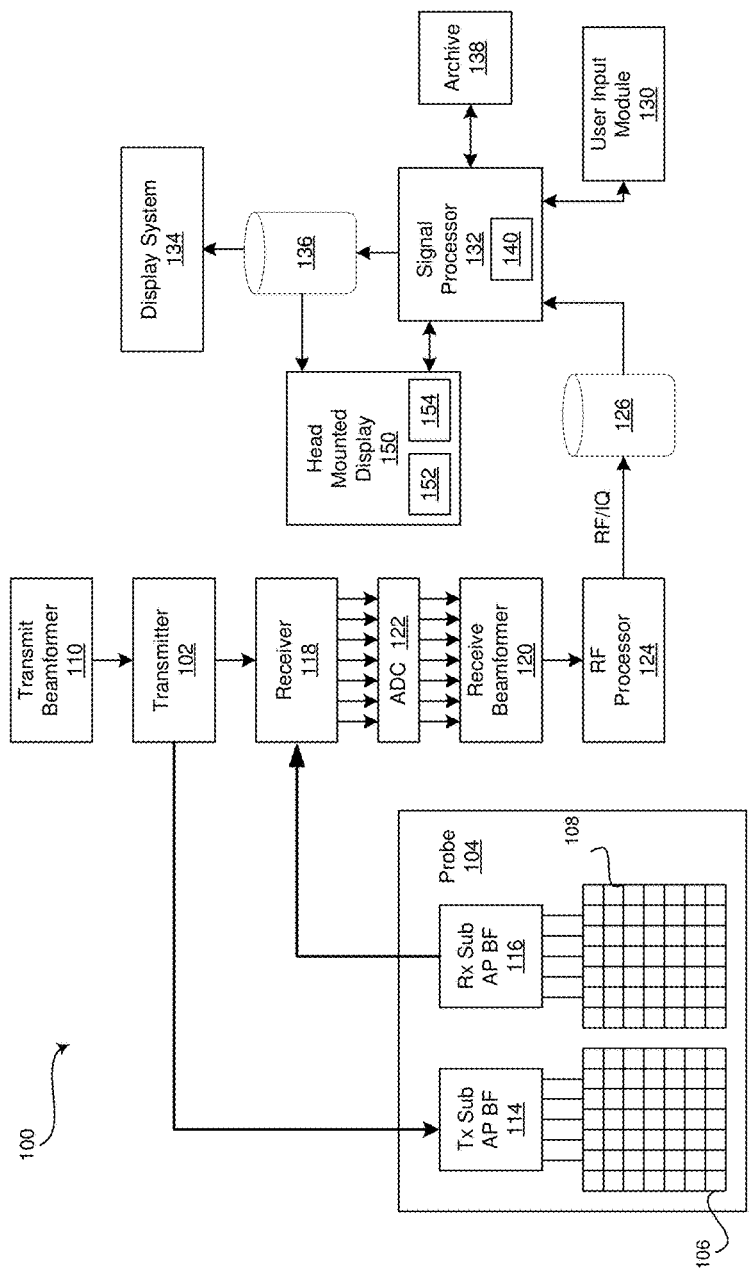
FIG. 1 is a block diagram of an exemplary ultrasound system that is operable to perform real-time volume rendering to provide enhanced visualization of ultrasound images at a head mounted display, in accordance with various embodiments.

Certain embodiments may be found in a method and system for providing enhanced visualization of ultrasound images at a head mounted display. For example, various aspects have the technical effect of providing volume rendering of ultrasound images substantially in real-time for presentation at a head mounted display. Moreover, certain embodiments have the technical effect of decreasing the volume rendering processing time by performing volume ray casting with a greater amount of rays cast near a user focal position and reducing the quantity of rays cast as the distance from the user focal position increases. Furthermore, various embodiments have the technical effect of decreasing the volume rendering processing time by increasing the sampling distance along the part of the ray that lies within the ultrasound image volume as the distance of the ray from the user focal position increases. Additionally, certain embodiments have the technical effect of avoiding aliasing by using a three-dimensional MIP map of the ultrasound data for performing volume ray casting. The MIP map may comprise multiple levels each having a different resolution. The graphics processing unit (GPU) may retrieve voxel data from the MIP mapped volume based at least in part on the local spacing between the rays and/or the ray sampling distance. The retrieved voxel data closer to the focus point may be at a MIP map level having a high resolution and the retrieved voxel data further away from the focus point may be at a coarser MIP map level having lower resolution.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments of the present disclosure. The following detailed description is, therefore, not to be taken in a limiting sense, and the scope of the present disclosure is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an embodiment," "one embodiment," "a representative embodiment," "an exemplary embodiment," "various embodiments," "certain embodiments," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode, CF-mode and/or sub-modes of CF such as TVI, Angio, B-flow, BMI, BMI_Angio, and in some cases also MM, CM, PW, TVD, CW where the "image" and/or "plane" includes a single beam or multiple beams.

Moreover, although certain embodiments in the foregoing description may describe the imaging modality and/or images in the context of ultrasound, for example, unless so claimed, the scope of various aspects of the present disclosure should not be limited to ultrasound imaging modalities and images and may additionally and/or alternatively be applicable to any suitable medical imaging modality and three-dimensional (3D) image, such as computed tomography, magnetic resonance, and the like.

Furthermore, the term processor or processing unit, as used herein, refers to any type of processing unit that can carry out the required calculations needed for the present disclosure, such as single or multi-core: CPU, Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 that is operable to perform real-time volume rendering to provide enhanced visualization of ultrasound images 400 at a head mounted display 150, in accordance with various embodiments. Referring to FIG. 1, there is shown an ultrasound system 100. The ultrasound system 100 comprises a transmitter 102, an ultrasound probe 104, a transmit beamformer 110, a receiver 118, a receive beamformer 120, a RF processor 124, a RF/IQ buffer 126, a user input module 130, a signal processor 132, an archive 138, an image buffer 136, a display system 134, and a head mounted virtual reality display (HMD) 150.

The transmitter 102 may comprise suitable logic, circuitry, interfaces and/or code that may be operable to drive an ultrasound probe 104. The ultrasound probe 104 may comprise a three dimensional (3D) array of piezoelectric elements. The ultrasound probe 104 may comprise a group of transmit transducer elements 106 and a group of receive transducer elements 108, that normally constitute the same elements.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116, and are then communicated to a receiver 118. The receiver 118 may comprise suitable logic, circuitry, interfaces and/or code that may be operable to receive and demodulate the signals from the receive sub-aperture beamformer 116. The demodulated analog signals may be communicated to one or more of the plurality of A/D converters 122.

The plurality of A/D converters 122 may comprise suitable logic, circuitry, interfaces and/or code that may be operable to convert the demodulated analog signals from the receiver 118 to corresponding digital signals. The plurality of A/D converters 122 are disposed between the receiver 118 and the receive beamformer 120. Notwithstanding, the present disclosure is not limited in this regard. Accordingly, in some embodiments of the disclosure, the plurality of A/D converters 122 may be integrated within the receiver 118.

The receive beamformer 120 may comprise suitable logic, circuitry, interfaces and/or code that may be operable to perform digital beamforming processing to, for example, sum the delayed channel signals received from the plurality of A/D converters 122 and output a beam summed signal. The resulting processed information may be converted back to corresponding RF signals. The corresponding output RF signals that are output from the receive beamformer 120 may be communicated to the RF processor 124. In accordance with some embodiments of the disclosure, the receiver 118, the plurality of A/D converters 122, and the beamformer 120 may be integrated into a single beamformer, which may be digital.

The RF processor 124 may comprise suitable logic, circuitry, interfaces and/or code that may be operable to demodulate the RF signals. In accordance with an embodiment of the disclosure, the RF processor 124 may comprise a complex demodulator (not shown) that is operable to demodulate the RF signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The user input module 130 may be utilized to input patient data, scan parameters, settings, configuration parameters, render settings, change scan mode, select an image display mode, and the like. In an exemplary embodiment of the disclosure, the user input module 130 may be operable to configure, manage and/or control operation of one or more components and/or modules in the ultrasound system 100. In this regard, the user input module 130 may be operable to configure, manage and/or control operation of transmitter 102, the ultrasound probe 104, the transmit beamformer 110, the receiver 118, the receive beamformer 120, the RF processor 124, the RF/IQ buffer 126, the user input module 130, the signal processor 132, the archive 138, the image buffer 136, the display system 134, and/or the head mounted virtual reality display (HMD) 150.

The head mounted virtual reality display (HMD) 150 may comprise suitable logic, circuitry, interfaces and/or code that may be operable to present ultrasound images 400 to a wearer of the HMD 150. The HMD 150 may comprise display units 152 for each eye. The display units 152 may be liquid crystal displays (LCDs), light emitting diodes (LEDs), liquid crystal on silicon (LCos), organic light emitting diodes (OLED), or any suitable displays. The HMD 150 may comprise sensors 154, such as head motion tracking sensors and eye tracking sensors. The head motion tracking sensors 154 may include gyroscopes, accelerometers, structured light systems, and the like for determining an orientation of the HMD 150. The eye tracking sensors 154 may be configured to determine a focal point (also referred to as a point of gaze) of the user of the HMD 150. As one example, the eye tracking sensors 154 may include lights, such as infrared lights, that may be reflected from the eye and sensed by an optical sensor to determine the focal point based at least in part on an eye position and/or rotation measurement. The HMD 150 may be communicatively coupled to the signal processor 132 to provide sensor feedback data from the head motion tracking and eye tracking sensors 154 and to receive ultrasound images 400 for display at the display units 152 based at least in part on the sensor feedback data.

The signal processor 132 may comprise suitable logic, circuitry, interfaces and/or code that may be operable to process ultrasound scan data (i.e., RF signal data or IQ data pairs) for generating ultrasound images for presentation on a display system 134 and/or the head mounted virtual reality display (HMD) 150. The signal processor 132 is operable to perform one or more processing operations according to a plurality of selectable ultrasound modalities on the acquired ultrasound scan data. In an exemplary embodiment of the disclosure, the signal processor 132 may be operable to perform volume rendering, compounding, motion tracking, and/or speckle tracking. Acquired ultrasound scan data may be processed in real-time during a scanning session as the echo signals are received. Additionally or alternatively, the ultrasound scan data may be stored temporarily in the RF/IQ buffer 126 and/or the archive 138 during a scanning session and processed in less than real-time in a live or off-line operation. The processed image data can be presented at the display system 134 and/or may be stored at the archive 138. The archive 138 may be a local archive, a Picture Archiving and Communication System (PACS), or any suitable device for storing images and related information. In the exemplary embodiment, the signal processor 132 may comprise and/or be communicatively coupled with a graphics processing unit (GPU) 140. The GPU 140 may be a separate discrete graphics board, integrated with the signal processor 132, or any suitable configuration.

The ultrasound system 100 may be operable to continuously acquire ultrasound scan data at a volume rate that is suitable for the imaging situation in question. Typical volume rates range from 10-30 volumes per second but may be lower or higher. The acquired ultrasound scan data may be displayed on the display system 134 and/or the HMD 150 at a display frame rate. For example, the display frame rate for ultrasound images presented at the HMD 150 may be at a steady rate in the range of 90-120 Hz to prevent motion sickness to the wearer of the HMD 150. An image buffer 136 is included for storing processed frames of acquired ultrasound scan data that are not scheduled to be displayed immediately. Preferably, the image buffer 136 is of sufficient capacity to store at least several seconds' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include and/or be communicatively coupled with a graphics processing unit (GPU) 140 that comprises suitable logic, circuitry, interfaces and/or code that may be operable to automatically generate a rendered view for presentation at an HMD 150 from 3D ultrasound data based at least in part on sensor data feedback provided from head motion tracking and eye tracking sensors 154 of the HMD 150. The sensor feedback data provided by the sensors 154 of the HMD 150 to the GPU 140 may relate to the position and orientation of the HMD 150 and the focal position of the eyes of the wearer of the HMD 150. The GPU 140 may receive 3D ultrasound data in real-time or near real-time as acquired by the ultrasound probe 104 and/or may retrieve 3D ultrasound data from an archive 138, such as a local archive, a Picture Archiving and Communication System (PACS), or any suitable device for storing images and related information.

The GPU 140 may comprise suitable logic, circuitry, interfaces and/or code that may be operable to perform volume rendering processing on the 3D ultrasound scan data 320. For example, the GPU 140 may perform volume ray casting on the 3D ultrasound scan data 320 to generate ultrasound images 400 for display at the display units 152 corresponding with each eye of a user of the HMD 150. In various embodiments, the GPU 140 may comprise suitable logic, circuitry, interfaces and/or code for generating a 3D MIP map from the 3D ultrasound scan data. The 3D MIP map may comprise several levels, each of the levels having a different resolution. For example, level zero may have a first highest resolution, level one may have a second highest resolution, level two may have a third highest resolution, and so on. The 3D MIP map may assist the GPU 140 in providing a volume rendered image without aliasing.

The GPU 140 may comprise suitable logic, circuitry, interfaces and/or code that may be operable to cast rays of sight at a predetermined pattern 300 through the 3D ultrasound scan data or 3D MIP map volume based at least in part on received sensor feedback data concerning the position and orientation of the HMD 150 and the focal position of the HMD wearer. For example, the sensor feedback data concerning the position and orientation of the HMD 150 may be used by the GPU 140 to identify a region of interest in the 3D ultrasound scan data or 3D MIP map volume. The sensor feedback data concerning the focal position of the HMD wearer may be used by the GPU 140 to case a pattern 300 of rays 310 through the 3D ultrasound scan data or 3D MIP map volume.

Figure 3:
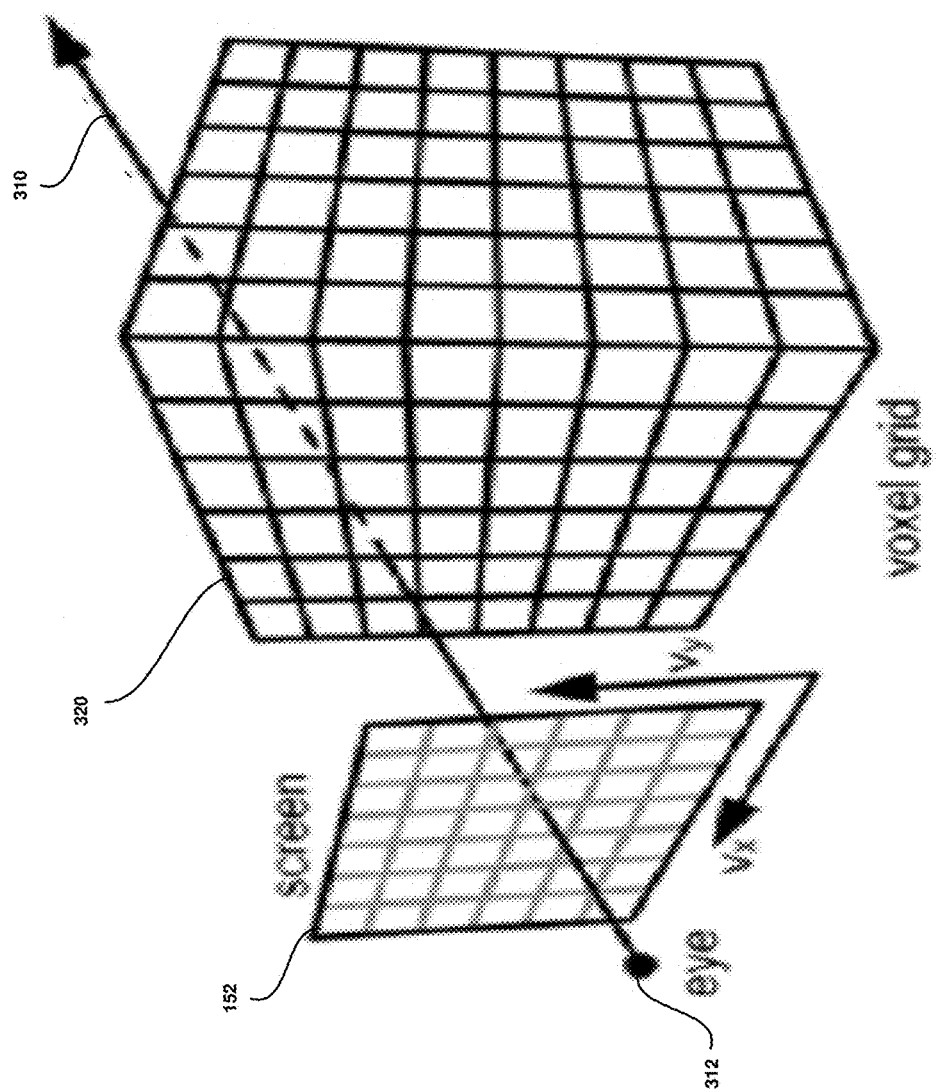
FIG. 3 is a perspective view of an exemplary ray of sight cast through an ultrasound image volume, in accordance with exemplary embodiments.

FIG. 3 is a perspective view of an exemplary ray of sight 310 cast through an ultrasound image volume 320, in accordance with exemplary embodiments. The ultrasound image volume 320 may be, for example, 3D ultrasound scan data acquired by the ultrasound probe 104, 3D ultrasound scan data retrieved from the archive 138, or a 3D MIP map volume generated by the GPU 140, among other things. The ray of sight 310 is cast from the perspective of the eye 312 of the HMD wearer through the ultrasound image volume 320 for a pixel of the final image to be displayed at the display unit 152 of the HMD 150. In various embodiments, a pattern 300 of rays 310 are cast from the eye 312 through the ultrasound image volume 320, each of the rays 310 corresponding with a pixel of the final image 400.

Figure 5:
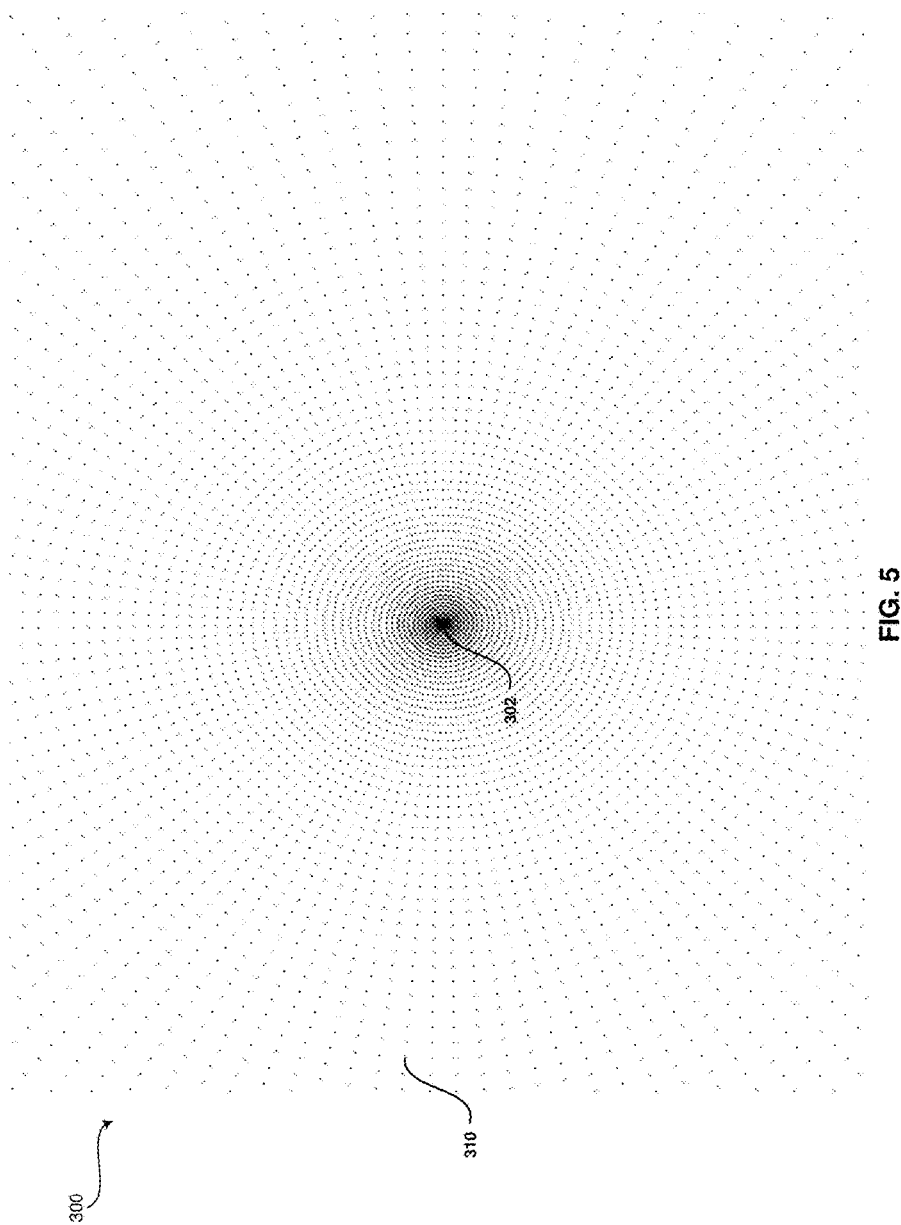
FIG. 5 is a top view of an exemplary pattern of rays cast through an ultrasound image volume, in accordance with exemplary embodiments.

FIG. 5 is a top view of an exemplary pattern 300 of rays 310 cast through an ultrasound image volume 320, in accordance with exemplary embodiments. Referring to FIG. 5, a greater amount of closely spaced rays 310 are cast at or near a focal point 302 of the wearer of the HMD 150 with larger spacing between rays 310 that are cast farther away from the focal point 302. The portions of the image having a greater amount of densely populated rays 310 provide a higher resolution than the portions of the image with a larger spacing between the rays 310. The wearer of the HMD 150 may not notice the difference in resolution because a typical user can perceive detail only at a small area surrounding the focal point. In various embodiments, the rays of sight 310 are cast such that the focal point of the user has a highest image resolution.

Figure 4:
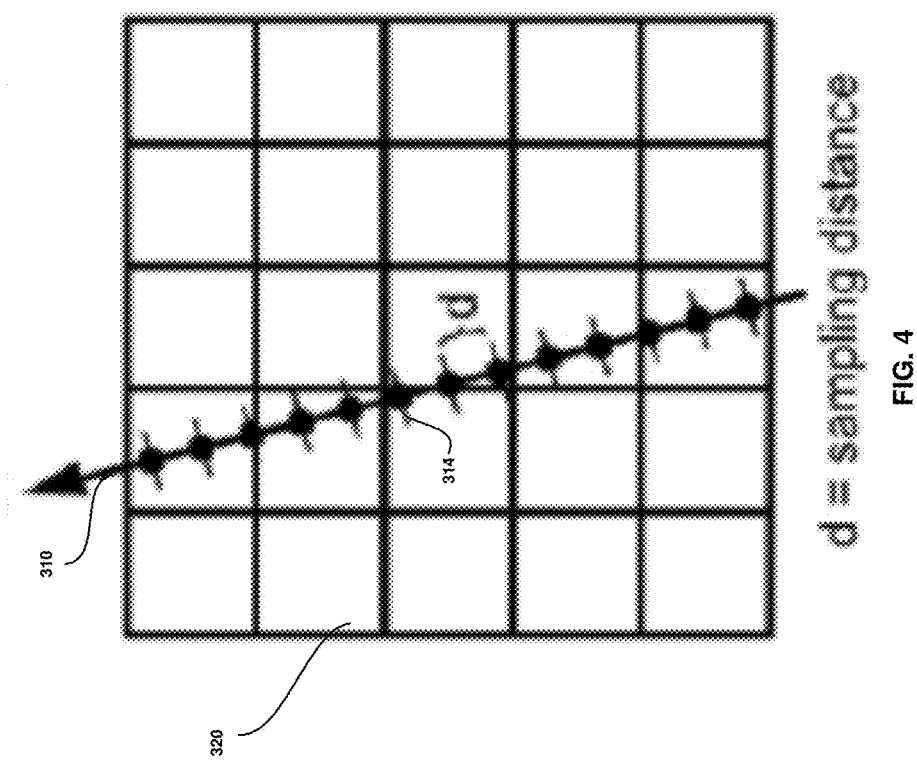
FIG. 4 is a top view of an exemplary sample points in an exemplary ray of sight cast through an ultrasound image volume, in accordance with exemplary embodiments.

Referring to FIGS. 3 and 5, each of the rays 310 cast through the ultrasound image volume 320 may be sampled at sampling points along the part of the ray 310 that lies within the volume 320. In various embodiments, the distance between sampling points may depend on the location of the ray 310 with respect to the focus point 302. For example, the sampling distance may be smaller the nearer the ray 310 is to the focus point 302. FIG. 4 is a top view of exemplary sample points 314 in an exemplary ray of sight 310 cast through an ultrasound image volume 320, in accordance with exemplary embodiments. Referring to FIG. 4, the ray of sight 310 passes through the ultrasound image volume 320. The ray of sight 310 may comprise a number of equidistant sampling points in the part of the ray 310 that lies within the volume 320. The sampling points 314 may be selected based at least in part on a sampling distance (d). The sampling distance (d) may be selected based at least in part on the position of the ray 310 with respect to the focus point 302. For example, rays 310 that are positioned closer to the focus point 302 may have a shorter sampling distance length and rays 310 that are positioned farther from the focus point 302 may have a longer sampling distance length. The shorter sampling distance lengths may provide a higher resolution than the longer sampling distance lengths. As shown in FIG. 4, the volume 320 may not be aligned with the ray of sight 310, and sampling points 314 may be located in between voxels. Accordingly, in various embodiments, the values of the samples 314 may be interpolated from surrounding voxels.

Figure 6:
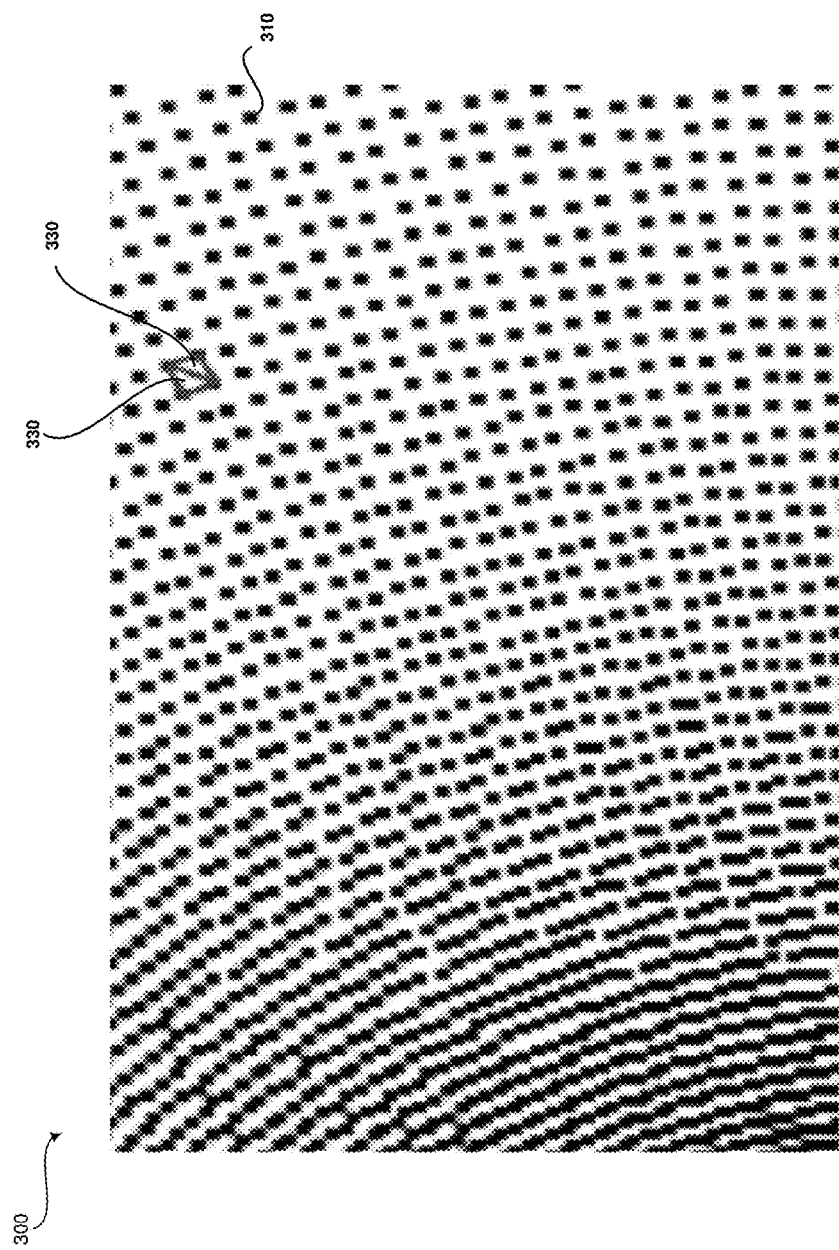
FIG. 6 is a top view of exemplary triangles of rays cast through an ultrasound image volume, in accordance with exemplary embodiments.

Referring again to FIGS. 1 and 3-5, after the rays 310 have been cast and the samples 314 selected, the samples 314 may be shaded to assign a color value. For example, a transfer function may retrieve an RGBA material color and can compute a gradient of illumination value for each sample. The gradient may represent the orientation of local surfaces within the volume 320. The samples may be shaded according to the surface orientation and location of the light source in the scene. The shaded samples may be composited along each ray 310 to assign a final color value to each ray 310 that is associated with a pixel of the final image 400. In various embodiments, the final color values of pixels associated with rays of sight 310 may be interpolated to assign color values to unassigned pixels. FIG. 6 is a top view of exemplary triangles 330 of rays 310 cast through an ultrasound image volume 320, in accordance with exemplary embodiments. Referring to FIG. 6, each of the rays 310 in the pattern 300 is associated with a pixel of the final image. The samples 314 of each ray 310 are shaded and composited to assign a final color value to the ray 310 or pixel. In order to fill in unused intermediate pixels, the GPU 140 may apply a shader from a graphics application programming interface (API), such as OpenGL, Direct3D, or any suitable graphics application. The shader may set up triangles 330 having one vertex per ray 310 position with an associated color value resulting from the ray casting. The final color value of each pixel 310 associated with a vertex may be interpolated when rendering the triangles to assign color values to the intermediate unassigned pixels. Still referring to FIG. 6, two exemplary triangles 330 are shown covering one specific patch of unassigned pixels between four vertices 310. In various embodiments, each unassigned patch in the image is assigned triangles 330 to fill in the intermediate pixels with color values.

Figure 7:
FIG. 7 is a screenshot of an exemplary image rendered by volume ray casting, in accordance with exemplary embodiments.

The GPU 140 may transmit the rendered image(s) to the HMD 150 for presentation at the display units 152 once the color values are assigned for each pixel of the image(s). FIG. 7 is a screenshot of an exemplary image 400 rendered by volume ray casting, in accordance with exemplary embodiments. Referring to FIG. 7, the rendered image 400 has a higher resolution around the focal point 402 and a lower resolution moving away from the focal point 402. In certain embodiments, performing volume ray casting on the 3D ultrasound scan data may result in some aliasing 404 being included in the rendered image 400.

To avoid aliasing 404, various embodiments perform volume ray casting on a 3D MIP map of the 3D ultrasound scan data. For example, the GPU 140 may generate a 3D MIP map from the ultrasound scan data. The 3D MIP map may comprise a plurality of levels, each of the levels having a different resolution. The GPU 140 may cast a ray 310 through a selected one of the 3D MIP map volume levels based at least in part on the location of the ray 310 with respect to the focal point 302, 402. For example, rays 310 located nearest the focal point 302, 402 may be cast through a level zero MIP map volume having a highest resolution. The GPU 140 may cast rays 310 farther from the focal point 302, 402 through a level one MIP map volume having a second highest resolution, a level two MIP map volume having a third highest resolution, and so on depending on the distance of the ray 310 from the focal point 302, 402. More specifically, higher resolution MIP map level volumes may be used closer to the focal point 302, 402 and lower resolution MIP map level volumes may be used when moving away from the focal point 302, 402. The GPU 140 may also approximate intermediate resolutions by interpolating between consecutive MIP map level volumes.

Figure 8:
FIG. 8 is a screenshot of an exemplary image rendered by volume ray casting and filtered to avoid aliasing, in accordance with exemplary embodiments.

FIG. 8 is a screenshot of an exemplary image 400 rendered by volume ray casting and filtered to avoid aliasing, in accordance with exemplary embodiments. Referring to FIG. 8, the aliasing 404 shown in FIG. 7 is no longer present. The aliasing 404 of FIG. 7 may be avoided, for example, by performing the volume ray casting using the MIP map volume to filter the ultrasound image data prior to casting the rays 310.

Figure 2:
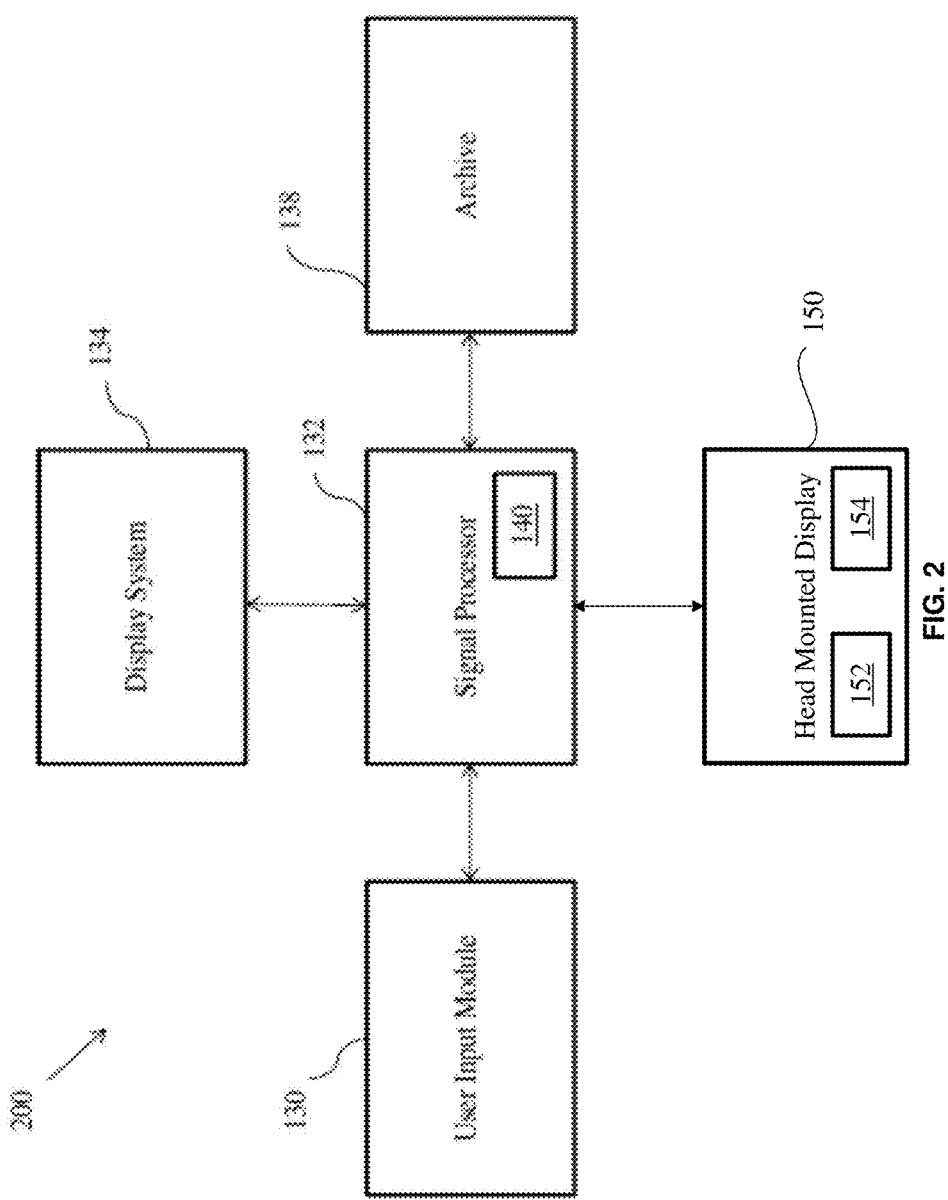
FIG. 2 is a block diagram of an exemplary medical workstation that is operable to perform real-time volume rendering to provide enhanced visualization of ultrasound images at a head mounted display, in accordance with certain embodiments.

FIG. 2 is a block diagram of an exemplary medical workstation 200 that is operable to perform real-time volume rendering to provide enhanced visualization of ultrasound images 400 at a head mounted display 150, in accordance with certain embodiments. In various embodiments, components of the medical workstation 200 may share various characteristics with components of the ultrasound system 100, as illustrated in FIG. 1 and described above. Referring to FIG. 2, the medical workstation 200 may comprise a head mounted virtual reality display (HMD) 150, a display system 134, a signal processor 132, an archive 138, and a user input module 130, among other things. Components of the medical workstation 200 may be implemented in software, hardware, firmware, and/or the like. The various components of the medical workstation 200 may be communicatively linked. Components of the medical workstation 200 may be implemented separately and/or integrated in various forms. For example, the display system 134 and the user input module 130 may be integrated as a touchscreen display.

The display system 134 may be a device capable of communicating visual information to a user. For example, a display system 134 may include a liquid crystal display, a light emitting diode display, and/or any suitable display or displays. The display system 134 can be operable to display information from the signal processor 132 and/or archive 138, such as medical images, or any suitable information.

The head mounted virtual reality display (HMD) 150 may be a wearable device capable of communicating visual information to a user. The HMD 150 may comprise display units 152 and sensors 154. The display units 152 may be liquid crystal displays (LCDs), light emitting diodes (LEDs), liquid crystal on silicon (LCos), organic light emitting diodes (OLED), or any suitable displays. The sensors 154 may include head motion tracking sensors and eye tracking sensors. The head motion tracking sensors 154 may include gyroscopes, accelerometers, structured light systems, and the like for determining an orientation of the HMD 150. The eye tracking sensors 154 may be configured to determine a focal point 302, 402 of the user of the HMD 150. The HMD 150 may be communicatively coupled to the signal processor 132 to provide sensor feedback data from the head motion tracking and eye tracking sensors 154 and to receive ultrasound images 400 for display at the display units 152 based at least in part on the sensor feedback data.

The signal processor 132 may be one or more central processing units, microprocessors, microcontrollers, and/or the like. The signal processor 132 may be an integrated component, or may be distributed across various locations, for example. The signal processor 132 may comprise and/or be communicatively coupled to a GPU 140, as described above with reference to FIG. 1. The GPU 140 may be capable of: (1) receiving 3D ultrasound image data from an archive 138, (2) optionally generating a 3D MIP map volume from the ultrasound image data, (3) receiving sensor feedback data identifying an HMD 150 position and user focal point 302 from HMD sensors 154, (4) performing volume ray casting on the 3D ultrasound image data or the 3D MIP map volume based on the received sensor feedback data, and (5) displaying the rendered ultrasound image 400 at display units 152 of the HMD 150, among other things. The signal processor 132 and/or GPU 140 may be capable of executing any of the method(s) and/or set(s) of instructions discussed herein in accordance with the various embodiments, for example.

The archive 138 may be one or more computer-readable memories integrated with the medical workstation 200 and/or communicatively coupled (e.g., over a network) to the medical workstation 200, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores 3D medical ultrasound image data, 3D MIP map volumes, and/or processor instructions for performing volume ray casting to generate a rendered image for display at the HMD 150, for example.

The user input module 130 may include any device(s) capable of communicating information from a user and/or at the direction of the user to the signal processor 132 of the medical workstation 200, for example. The user input module 130 may include a mousing device, keyboard, touch panel, camera, buttons, switches, voice recognition, and/or any other device capable of receiving a user directive.

Figure 9:
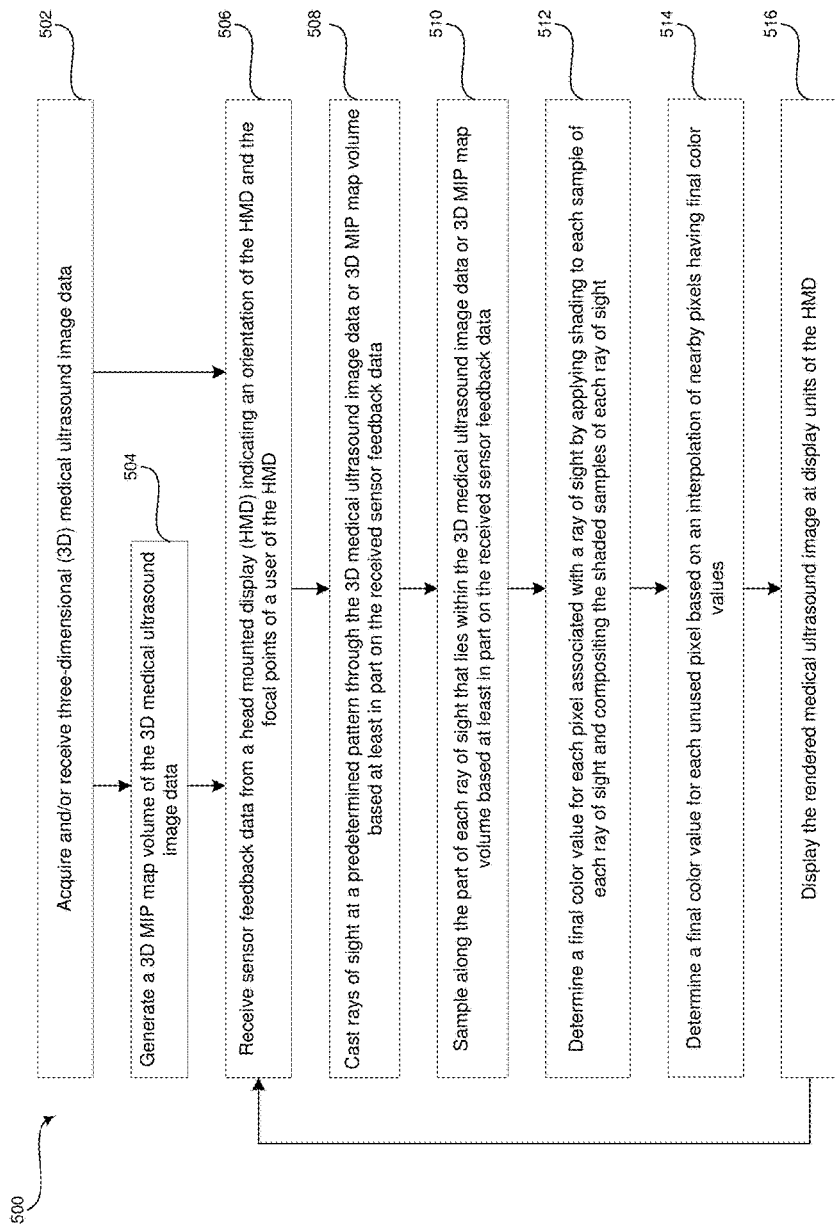
FIG. 9 is a flow chart illustrating exemplary steps that may be utilized for performing real-time volume rendering to provide enhanced visualization of ultrasound images at a head mounted display, in accordance with various embodiments.

FIG. 9 is a flow chart 500 illustrating exemplary steps 502-516 that may be utilized for performing real-time volume rendering to provide enhanced visualization of ultrasound images 400 at a head mounted display 150, in accordance with various embodiments. Referring to FIG. 5, there is shown a flow chart 500 comprising exemplary steps 502 through 516. Certain embodiments of the present disclosure may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

In step 502, the signal processor 132 may receive 3D medical ultrasound image data. For example, an ultrasound system 100 may acquire 3D ultrasound data that is provided to the signal processor 132 as described above with regard to FIG. 1. As another example, the signal processor 132 of the ultrasound system 100 or a medical workstation 200 may retrieve the 3D medical ultrasound image data from an archive 138.

In step 504, a GPU 140 may generate a 3D MIP map volume of the 3D medical ultrasound image data. For example, the 3D MIP map volume may comprise several levels of ultrasound image volumes, each having a different resolution. In various embodiments, a 3D volume at a particular resolution level may be retrieved to perform volume ray casting as described below.

In step 506, the GPU 140 may receive sensor feedback data from sensors 154 of a head mounted virtual reality display (HMD) 150. For example, the HMD 150 may comprise head motion tracking sensors 154 for determining an orientation of the HMD 150 and eye tracking sensors 154 for determining a focal point 302, 402 of the user of the HMD 150. The GPU 140 may select a region of interest in the 3D medical ultrasound image data or the 3D MIP map volume based on the received sensor feedback data specifying the orientation of the HMD 150. The GPU 140 may perform volume ray casting as described below based at least in part on the focal point 302, 402 identified by the received sensor feedback data.

In step 508, the GPU 140 may cast rays of sight 310 at a predetermined pattern 300 through the 3D medical ultrasound image data or 3D MIP map volume 320 based at least in part on the received sensor feedback data. For example, each of the rays of sight 310 may be associated with a pixel of a final rendered image 400. The final rendered image 400 may have pixels associated with the rays 310 and unassigned pixels not associated with any of the rays 310. The rays 310 may be spaced based at least in part on the proximity to the focal point 302, 402. For example, rays 310 located closer to the focal point 302, 402 may be more densely populated such that the rays 310 are spaced closer to together. The rays 310 may be more sparsely populated with a larger spacing between the rays 310 as the location of the rays 310 moves farther away from the focal point 302, 402 as shown, for example, in the ray of sight pattern 300 illustrated in FIG. 5.

In step 510, the GPU 140 may select samples 314 along the part of each ray 310 that lies within the 3D medical ultrasound image data or 3D MIP map volume 320 based at least in part on the received sensor feedback data. For example, the GPU 140 may use the focal point 302, 402 identified by the sensor feedback data to select the distance (d) between samples 314 of a ray 310. In various embodiments, the samples 314 of rays 310 that are at or near the focal point 302, 402 may have a shorter selected sampling distance to provide a higher image resolution and the sampling distance selected for rays 310 farther away from the focal point 302, 402 may have a larger sampling distance to provide a lower image resolution.

In step 512, the GPU 140 may determine a final color value for each pixel associated with a ray of sight 310 by applying shading to each sample 314 of each ray of sight 310 and compositing the shaded samples 314 of each ray of sight 310.

In step 514, the GPU 140 may determine a final color value for each unused pixel based on an interpolation of nearby pixels having final color values. For example, the final color values corresponding with each of the unassigned pixels may be determined by interpolating the final color values corresponding with nearby pixels of associated rays 310. In various embodiments, the interpolating the final color values corresponding with nearby pixels may include applying a shader from a graphics application, such as OpenGL, Direct3D, or any suitable graphics application. The shader may set-up triangles 330 having vertices corresponding with the nearby pixels associated with the rays 310. The final color values of the nearby pixels 310 associated with the vertices may be interpolated to determine the final color values of unassigned pixels within each of the triangles 330.

In step 516, the display units 152 of the HMD 150 may display the rendered medical ultrasound image 400. For example, an image 400 may be rendered for each eye 312 of the HMD 150 wearer and displayed at a display unit 152 associated with one of the wearer's eyes 312. The HMD 150 may be communicatively coupled with the GPU 140 such that the volume rendered image(s) 400 may be provided by the GPU 140 to the display units 152 of the HMD 150.

Aspects of the present disclosure provide a method 500 and system 100, 200 for performing real-time volume rendering to provide enhanced visualization of ultrasound images 400 at a head mounted display 150. In accordance with various embodiments, the method 500 comprises receiving 506, by a processor 132, 140, sensor feedback data indicating at least one focal point 302, 402 of a user of a head mounted display (HMD) 150. The method 500 comprises casting 508, by the processor 132, 140, a plurality of rays 310 at a predetermined pattern 300 through an ultrasound image volume 320 based at least in part on the sensor feedback data. Each of the plurality of rays 310 is associated with a pixel of a final rendered image 400. The final rendered image 400 has a first plurality of pixels associated with the plurality of rays 310 and a second plurality of unassociated pixels. The plurality of rays 310 comprises a first portion cast at or near the at least one focal point 302, 402 and a second portion that is cast farther away from the at least one focal point 302, 402 than the first portion. A first spacing between rays of the first portion of the plurality of rays 310 is less than a second spacing between rays of the second portion of the plurality of rays 310. The method 500 comprises determining 512, by the processor 132, 140, final color values corresponding with each of the first plurality of pixels associated with the plurality of rays 310. The method 500 comprises determining 514, by the processor 132, 140, final color values corresponding with each of the second plurality of unassociated pixels of the final rendered image 400. The method 500 comprises displaying 516, by the HMD 150, the final rendered image 400.

In various embodiments, the final color values corresponding with each of the second plurality of unassociated pixels are determined by interpolating the final color values corresponding with nearby pixels of the first plurality of pixels associated with the plurality of rays 310. In certain embodiments, the interpolating the final color values corresponding with nearby pixels comprises applying a shader from a graphics application. In a representative embodiment, the shader sets up triangles 330 having vertices 310 associated with the nearby pixels of the first plurality of pixels associated with the plurality of rays 310. The final color values of the nearby pixels 310 associated with the vertices are interpolated to determine the final color values of pixels within each of the triangles 330 corresponding with the second plurality of unassociated pixels.

In certain embodiments, the ultrasound image volume 320 is one or both of three-dimensional (3D) medical ultrasound image data and a 3D MIP map volume generated by the processor 132, 140 from the 3D medical ultrasound image data. The 3D MIP map volume comprises a plurality of levels of image volumes, each of the levels having a different image resolution. In a representative embodiment, the method 500 comprises retrieving 502, by the processor 132, 140, the ultrasound image volume 320 from an archive 138. In certain embodiments, the method 500 comprises acquiring 502, by an ultrasound probe 104, the 3D medical ultrasound image data. The method 500 comprises receiving 502, by the processor 132, 140, the 3D medical ultrasound image data from the probe 104. The method 500 comprises generating 504, by the processor 132, 140, the 3D MIP map volume from the 3D medical ultrasound image data. In various embodiments, the ultrasound image volume 320 is the 3D MIP map volume. The first portion of the plurality of rays 310 is cast through a first level of the plurality of levels of image volumes of the 3D MIP map volume. The second portion of the plurality of rays 310 is cast through a second level of the plurality of levels of image volumes of the 3D MIP map volume. The first level has a higher image resolution than the second level.

In a representative embodiment, the method 500 comprises sampling 510, by the processor 132, 140, along a part of each of the plurality of rays 310 that lies within the ultrasound image volume 320 based at least in part on the sensor feedback data. The sampling 510 comprises selecting samples 314 at an equidistant sampling distance (d). The first portion of the plurality of rays 310 has a first sampling distance. The second portion of the plurality of rays 310 has a second sampling distance. The first sampling distance is smaller than the second sampling distance. In certain embodiments, the final color values corresponding with each of the first plurality of pixels associated with the plurality of rays 310 is determined 512 by applying shading to each of the samples 314 of each of the plurality of rays 310 and compositing the shaded samples 314 of each of the plurality of rays 310.

Various embodiments provide a system 100, 200 for performing real-time volume rendering to provide enhanced visualization of ultrasound images 400 at a head mounted display 150. The system 100, 200 comprises a head mounted display (HMD) 150 configured to provide sensor feedback data indicating at least one focal point 302, 402 of a user. The HMD 150 is configured to display a final rendered image 400. The system 100, 200 comprises a processor 132, 140 configured to receive the sensor feedback data. The processor 132, 140 is configured to cast a plurality of rays 310 at a predetermined pattern 300 through an ultrasound image volume 320 based at least in part on the sensor feedback data. Each of the plurality of rays 310 is associated with a pixel of the final rendered image 400. The final rendered image 400 has a first plurality of pixels associated with the plurality of rays 310 and a second plurality of unassociated pixels. The plurality of rays 310 comprises a first portion cast at or near the at least one focal point 302, 402 and a second portion that is cast farther away from the at least one focal point 302, 402 than the first portion. A first spacing between rays of the first portion of the plurality of rays 310 is less than a second spacing between rays of the second portion of the plurality of rays 310. The processor 132, 140 is configured to determine final color values corresponding with each of the first plurality of pixels associated with the plurality of rays 310. The processor 132, 140 is configured to determine final color values corresponding with each of the second plurality of unassociated pixels of the final rendered image 400.

In certain embodiments, the processor 132, 140 is configured to determine the final color values corresponding with each of the second plurality of unassociated pixels by applying a shader from a graphics application to interpolate the final color values corresponding with nearby pixels of the first plurality of pixels associated with the plurality of rays 310. The shader sets up triangles 330 having vertices associated with the nearby pixels of the first plurality of pixels associated with the plurality of rays 310. The final color values of the nearby pixels 310 associated with the vertices are interpolated to determine the final color values of pixels within each of the triangles 330 corresponding with the second plurality of unassociated pixels. In various embodiments, the ultrasound image volume 320 is a 3D MIP map volume generated by the processor 132, 140 from 3D medical ultrasound image data. The 3D MIP map volume comprises a plurality of levels of image volumes, each of the levels having a different image resolution. The processor 132, 140 is configured to cast the first portion of the plurality of rays 310 through a first level of the plurality of levels of image volumes of the 3D MIP map volume 320. The processor 132, 140 is configured to cast the second portion of the plurality of rays 310 through a second level of the plurality of levels of image volumes of the 3D MIP map volume 320. The first level has a higher image resolution than the second level.

In a representative embodiment, the processor 132, 140 is configured to sample along a part of each of the plurality of rays 310 that lies within the ultrasound image volume 320 based at least in part on the sensor feedback data. The processor 132, 140 is configured to sample by selecting samples 314 at an equidistant sampling distance (d). The first portion of the plurality of rays 310 has a first sampling distance. The second portion of the plurality of rays 310 has a second sampling distance. The first sampling distance is smaller than the second sampling distance. The processor 132, 140 is configured to determine the final color values corresponding with each of the first plurality of pixels associated with the plurality of rays 310 by applying shading to each of the samples 314 of each of the plurality of rays 310 and compositing the shaded samples 314 of each of the plurality of rays 310.

Certain embodiments provide a non-transitory computer readable medium having stored thereon, a computer program having at least one code section. The at least one code section is executable by a machine for causing the machine to perform steps. The steps 500 include receiving 506 sensor feedback data indicating at least one focal point 302, 402 of a user of a head mounted display (HMD) 150. The steps 500 comprise casting 508 a plurality of rays 310 at a predetermined pattern 300 through an ultrasound image volume 3620 based at least in part on the sensor feedback data. Each of the plurality of rays 310 is associated with a pixel of a final rendered image 400. The final rendered image 400 has a first plurality of pixels associated with the plurality of rays 310 and a second plurality of unassociated pixels. The plurality of rays 310 comprises a first portion cast at or near the at least one focal point 302, 402 and a second portion that is cast farther away from the at least one focal point 302, 402 than the first portion. A first spacing between rays of the first portion of the plurality of rays 310 is less than a second spacing between rays of the second portion of the plurality of rays 310. The steps 500 comprise determining 512 final color values corresponding with each of the first plurality of pixels associated with the plurality of rays 310. The steps 500 comprise determining 514 final color values corresponding with each of the second plurality of unassociated pixels of the final rendered image 400. The steps 500 comprise displaying 516 the final rendered image 400 at the HMD 150.

In various embodiments, the final color values corresponding with each of the second plurality of unassociated pixels are determined by interpolating the final color values corresponding with nearby pixels of the first plurality of pixels associated with the plurality of rays 310. The interpolating the final color values corresponding with nearby pixels comprises applying a shader from a graphics application. The shader sets up triangles 330 having vertices associated with the nearby pixels of the first plurality of pixels associated with the plurality of rays 310. The final color values of the nearby pixels 310 associated with the vertices are interpolated to determine the final color values of pixels within each of the triangles 330 corresponding with the second plurality of unassociated pixels. In certain embodiments, the ultrasound image volume 320 is a 3D MIP map volume generated from 3D medical ultrasound image data. The 3D MIP map volume comprises a plurality of levels of image volumes, each of the levels having a different image resolution. The first portion of the plurality of rays 310 is cast through a first level of the plurality of levels of image volumes of the 3D MIP map volume 320. The second portion of the plurality of rays 310 is cast through a second level of the plurality of levels of image volumes of the 3D MIP map volume 320. The first level has a higher image resolution than the second level.

In a representative embodiment, the steps 500 comprise sampling 510 along a part of each of the plurality of rays 310 that lies within the ultrasound image volume 320 based at least in part on the sensor feedback data. The sampling 510 comprises selecting samples 314 at an equidistant sampling distance (d). The first portion of the plurality of rays 310 has a first sampling distance. The second portion of the plurality of rays 310 has a second sampling distance. The first sampling distance is smaller than the second sampling distance. In various embodiments, the final color values corresponding with each of the first plurality of pixels associated with the plurality of rays 310 is determined by applying shading to each of the samples 314 of each of the plurality of rays 310 and compositing the shaded samples 314 of each of the plurality of rays 310.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments of the disclosure may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for performing real-time volume rendering to provide enhanced visualization of ultrasound images at a head mounted display.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

The present disclosure may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
   receiving, by a processor, sensor feedback data indicating at least one focal point of a user of a head mounted display (HMD);
   casting, by the processor, a plurality of rays at a predetermined pattern through an ultrasound image volume based at least in part on the sensor feedback data, wherein:
   each of the plurality of rays is associated with a pixel of a final rendered image, the final rendered image having a first plurality of pixels associated with the plurality of rays and a second plurality of unassociated pixels,
   the plurality of rays comprises a first portion cast at or near the at least one focal point and a second portion that is cast farther away from the at least one focal point than the first portion, and
   a first spacing between rays of the first portion of the plurality of rays is less than a second spacing between rays of the second portion of the plurality of rays;
   determining, by the processor, final color values corresponding with each of the first plurality of pixels associated with the plurality of rays;
   determining, by the processor, final color values corresponding with each of the second plurality of unassociated pixels of the final rendered image; and
   displaying, by the HMD, the final rendered image.

2. The method according to claim 1, wherein the final color values corresponding with each of the second plurality of unassociated pixels are determined by interpolating the final color values corresponding with nearby pixels of the first plurality of pixels associated with the plurality of rays.

3. The method according to claim 2, wherein the interpolating the final color values corresponding with nearby pixels comprises applying a shader from a graphics application.

4. The method according to claim 3, wherein the shader sets up triangles having vertices associated with the nearby pixels of the first plurality of pixels associated with the plurality of rays, and wherein the final color values of the nearby pixels associated with the vertices are interpolated to determine the final color values of pixels within each of the triangles corresponding with the second plurality of unassociated pixels.

5. The method according to claim 1, wherein the ultrasound image volume is one or both of:
three-dimensional (3D) medical ultrasound image data, and
a 3D MIP map volume generated by the processor from the 3D medical ultrasound image data, wherein the 3D MIP map volume comprises a plurality of levels of image volumes, each of the levels having a different image resolution.

6. The method according to claim 5, comprising retrieving, by the processor, the ultrasound image volume from an archive.

7. The method according to claim 5, comprising a plurality of:
acquiring, by an ultrasound probe, the 3D medical ultrasound image data,
receiving, by the processor, the 3D medical ultrasound image data from the probe, and
generating, by the processor, the 3D MIP map volume from the 3D medical ultrasound image data.

8. The method according to claim 5, wherein the ultrasound image volume is the 3D MIP map volume, and wherein:
the first portion of the plurality of rays is cast through a first level of the plurality of levels of image volumes of the 3D MIP map volume,
the second portion of the plurality of rays is cast through a second level of the plurality of levels of image volumes of the 3D MIP map volume, and
the first level has a higher image resolution than the second level.

9. The method according to claim 1, comprising sampling, by the processor, along a part of each of the plurality of rays that lies within the ultrasound image volume based at least in part on the sensor feedback data, wherein:
the sampling comprises selecting samples at an equidistant sampling distance,
the first portion of the plurality of rays has a first sampling distance,
the second portion of the plurality of rays has a second sampling distance, and
the first sampling distance is smaller than the second sampling distance.

10. The method according to claim 9, wherein the final color values corresponding with each of the first plurality of pixels associated with the plurality of rays is determined by applying shading to each of the samples of each of the plurality of rays and compositing the shaded samples of each of the plurality of rays.

11. A system comprising:
a head mounted display (HMD) configured to:
provide sensor feedback data indicating at least one focal point of a user; and
display a final rendered image; and
a processor configured to:
receive the sensor feedback data;
cast a plurality of rays at a predetermined pattern through an ultrasound image volume based at least in part on the sensor feedback data, wherein:
each of the plurality of rays is associated with a pixel of the final rendered image, the final rendered image having a first plurality of pixels associated with the plurality of rays and a second plurality of unassociated pixels,
the plurality of rays comprises a first portion cast at or near the at least one focal point and a second portion that is cast farther away from the at least one focal point than the first portion, and
a first spacing between rays of the first portion of the plurality of rays is less than a second spacing between rays of the second portion of the plurality of rays;
determine final color values corresponding with each of the first plurality of pixels associated with the plurality of rays; and
determine final color values corresponding with each of the second plurality of unassociated pixels of the final rendered image.

12. The system according to claim 11, wherein:
the processor is configured to determine the final color values corresponding with each of the second plurality of unassociated pixels by applying a shader from a graphics application to interpolate the final color values corresponding with nearby pixels of the first plurality of pixels associated with the plurality of rays,
the shader sets up triangles having vertices associated with the nearby pixels of the first plurality of pixels associated with the plurality of rays, and
the final color values of the nearby pixels associated with the vertices are interpolated to determine the final color values of pixels within each of the triangles corresponding with the second plurality of unassociated pixels.

13. The system according to claim 11, wherein:
the ultrasound image volume is a 3D MIP map volume generated by the processor from 3D medical ultrasound image data,
the 3D MIP map volume comprises a plurality of levels of image volumes, each of the levels having a different image resolution,
the processor is configured to cast the first portion of the plurality of rays through a first level of the plurality of levels of image volumes of the 3D MIP map volume,
the processor is configured to cast the second portion of the plurality of rays through a second level of the plurality of levels of image volumes of the 3D MIP map volume, and
the first level has a higher image resolution than the second level.

14. The system according to claim 11, wherein the processor is configured to sample along a part of each of the plurality of rays that lies within the ultrasound image volume based at least in part on the sensor feedback data, wherein:
the processor is configured to sample by selecting samples at an equidistant sampling distance,
the first portion of the plurality of rays has a first sampling distance,
the second portion of the plurality of rays has a second sampling distance, and
the first sampling distance is smaller than the second sampling distance.

15. The system according to claim 14, wherein the processor is configured to determine the final color values corresponding with each of the first plurality of pixels associated with the plurality of rays by applying shading to each of the samples of each of the plurality of rays and compositing the shaded samples of each of the plurality of rays.

16. A non-transitory computer readable medium having stored thereon, a computer program having at least one code section, the at least one code section being executable by a machine for causing the machine to perform steps comprising:
- receiving sensor feedback data indicating at least one focal point of a user of a head mounted display (HMD);
- casting a plurality of rays at a predetermined pattern through an ultrasound image volume based at least in part on the sensor feedback data, wherein:
  - each of the plurality of rays is associated with a pixel of a final rendered image, the final rendered image having a first plurality of pixels associated with the plurality of rays and a second plurality of unassociated pixels,
  - the plurality of rays comprises a first portion cast at or near the at least one focal point and a second portion that is cast farther away from the at least one focal point than the first portion, and
  - a first spacing between rays of the first portion of the plurality of rays is less than a second spacing between rays of the second portion of the plurality of rays;
- determining final color values corresponding with each of the first plurality of pixels associated with the plurality of rays;
- determining final color values corresponding with each of the second plurality of unassociated pixels of the final rendered image; and
- displaying the final rendered image at the HMD.

17. The non-transitory computer readable medium according to claim 16, wherein:
- the final color values corresponding with each of the second plurality of unassociated pixels are determined by interpolating the final color values corresponding with nearby pixels of the first plurality of pixels associated with the plurality of rays,
- the interpolating the final color values corresponding with nearby pixels comprises applying a shader from a graphics application,
- the shader sets up triangles having vertices associated with the nearby pixels of the first plurality of pixels associated with the plurality of rays, and
- the final color values of the nearby pixels associated with the vertices are interpolated to determine the final color values of pixels within each of the triangles corresponding with the second plurality of unassociated pixels.

18. The non-transitory computer readable medium according to claim 16, wherein:
- the ultrasound image volume is a 3D MIP map volume generated from 3D medical ultrasound image data,
- the 3D MIP map volume comprises a plurality of levels of image volumes, each of the levels having a different image resolution,
- the first portion of the plurality of rays is cast through a first level of the plurality of levels of image volumes of the 3D MIP map volume,
- the second portion of the plurality of rays is cast through a second level of the plurality of levels of image volumes of the 3D MIP map volume, and
- the first level has a higher image resolution than the second level.

19. The non-transitory computer readable medium according to claim 16, comprising sampling along a part of each of the plurality of rays that lies within the ultrasound image volume based at least in part on the sensor feedback data, wherein:
- the sampling comprises selecting samples at an equidistant sampling distance,
- the first portion of the plurality of rays has a first sampling distance,
- the second portion of the plurality of rays has a second sampling distance, and
- the first sampling distance is smaller than the second sampling distance.

20. The non-transitory computer readable medium according to claim 19, wherein the final color values corresponding with each of the first plurality of pixels associated with the plurality of rays is determined by applying shading to each of the samples of each of the plurality of rays and compositing the shaded samples of each of the plurality of rays.

* * * * *